United States Patent [19]
Kikumoto et al.

[11] Patent Number: 4,966,145
[45] Date of Patent: Oct. 30, 1990

[54] AUTOMATIC BODY TEMPERATURE ADJUSTER

[75] Inventors: Makoto Kikumoto; Masakazu Moroto, both of Hirakata; Masato Osumi, Moriguchi, all of Japan

[73] Assignees: Agency of Industrial Science & Technology; Ministry of International Trade & Industry, both of Tokyo, Japan

[21] Appl. No.: 403,034

[22] Filed: Sep. 1, 1989

Related U.S. Application Data

[63] Continuation of Ser. No. 168,415, Mar. 15, 1988, abandoned.

[30] Foreign Application Priority Data

Mar. 19, 1987 [JP] Japan .................................. 62-62482

[51] Int. Cl.$^5$ .............................................. A61F 7/00
[52] U.S. Cl. .................................... 128/377; 128/399;
128/400; 297/180; 297/DIG. 4; 280/304.1;
165/46
[58] Field of Search ................ 128/376, 33, 399, 400,
128/377; 297/180, DIG. 4; 280/647, 242.1,
304.1; 5/453; 165/46

[56] References Cited

U.S. PATENT DOCUMENTS

| 2,722,266 | 11/1955 | Kersten | 297/180 |
| 3,136,577 | 6/1964 | Richard | 128/377 |
| 3,507,321 | 4/1970 | Palma | 128/400 |
| 4,306,747 | 12/1981 | Moss | 297/180 |
| 4,694,521 | 9/1987 | Tominaga | 5/453 |
| 4,773,494 | 9/1988 | Anderson | 297/180 |
| 4,844,072 | 7/1989 | Frach et al. | 128/400 |

FOREIGN PATENT DOCUMENTS 61-100243 5/1986 Japan .

Primary Examiner—Edward M. Coven
Assistant Examiner—Mark S. Graham
Attorney, Agent, or Firm—Oblon, Spivak, McClelland, Maier & Neustadt

[57] ABSTRACT

An automatic body temperature adjuster is disclosed, in which a cold storage material and a coolant medium circulation path for cooling the material are built into the seat and/or the back support of a wheelchair, the coolant medium circulation path being capable of being coupled by coupler means to cold supply means of the heat exchange means. Prior to use of the automatic body temperature adjuster, the cold storage material in the seat and/or back support is cooled, i.e., cold is stored in the material, by operating the cold supply means. When the adjuster is in use, the coupler means may instead be connected to a cold supply section in a cover worn by the user.

7 Claims, 5 Drawing Sheets

AUTOMATIC BODY TEMPERATURE ADJUSTER

This is a continuation of application Ser. No. 168,415 filed on Mar. 15, 1988 now abandoned.

BACKGROUND OF THE INVENTION

1. Field of the Invention

This invention relates to an automatic body temperature adjuster and, more particularly, to an automatic body temperature controller for automatically controlling the temperature of a person who has lost his or her body temperature control function because of, for example, damage to the spinal cord.

2. Prior Art Statement

In a person who has lost his or her body temperature control function because of, for example, damage to the spinal cord, heat generated by metabolism is not sufficiently dissipated outside of the body when the ambient atmospheric temperature and/or relative humidity is high, such as in summer. In this case, the heat is retained in the body, leading to heat retention. In extreme cases, the heat retention may very seriously disrupt the physiological functions.

To prevent the heat retention, heat is forcibly extracted from the person's body. The usual practice is to put the person in an air conditioned room. However, in addition to being an expensive solution, this method confines the person to an air conditioned building or room.

Japanese Patent Public Disclosure Sho No. 61(1986)100243 discloses a mobile automatic body temperature adjuster which is denoted in FIG. 8 by the symbol Ca. As the adjuster is mobile, the user is not confined in any particular place.

This automatic body temperature adjuster Ca comprises a heat or cold storage material; a circulation means including a circulation pump, a supply section for supplying heat or cold to the heat or cold storage material and a receiving section for receiving heat or cold from a heat or cold source, which are connected to form a closed circuit for circulation of a medium from the receiving section to the supply section through the circulation pump; a sensor for sensing temperature of the heat or cold storage material; control means for producing a signal for controlling the amount of heat or cold received by the heat or cold receiving section according to a signal from the sensor; and a holding member for holding the heat or cold storage material and sensor in contact with the user's body and also holding the heat or cold supply section in contact with the heat or cold storage material.

As shown in FIG. 8, the aforementioned adjuster comprises a liquid cooler 9a which includes a DC compressor 6a, a condenser 7a, a capillary tube 8a and a heat exchanger 1a and serves as a cold source, a cold medium circulation path 30a which connects the heat exchanger 1a, a three-way valve 10a, a circulation pump 4a and a cold supply section 5a to form a closed circuit and also includes a bypass 31a bypassing the heat exchanger 1a and connecting with the remaining port of the three-way valve 10a, a controller 11a, a sensor 13a for sensing the temperature of the user's body, and a cold (heat) storage member 14a. The cold storage member 14a is filled with a cold storage material (e.g., an aqueous solution of sodium chloride). The individual components of the automatic body temperature adjuster Ca are driven by a rechargeable battery.

The liquid cooler 9a conducts a refrigerating cycle using a coolant gas medium. The coolant gas medium is compressed in the DC compressor 6a, causing it to be increased in temperature and pressure. It is then supplied to the condenser 7a to be cooled and liquefied. The liquefied coolant medium is passed through the capillary tube 8a for pressure reduction and is then supplied to the heat exchanger 1a where it evaporates, thus extracting heat from its surroundings and providing a cooling function.

Likewise, the heat exchanger 1a, the three-way valve 10a, the circulation pump 4a, the path of the cold supply section 5a and the bypass 31a constitute a coolant medium circulation path 30a using a liquid (e.g., water) as a coolant medium. The circulating coolant medium which has been cooled by the heat exchanger 1a passes through the three-way valve 10a and is supplied by the circulation pump 4a to the cold supply section 5a. As it circulates through the cold supply section 5a, it extracts heat from the body of the user whose body temperature is to be controlled. Then, part of it is circulated to the heat exchanger 1a and the remainder is circulated to the bypass 31a. By varying the ratio of the circulating coolant medium that is sent to the heat exchanger 1a for cooling to the medium that flows through the bypass 31a, it is possible to control the temperature of the circulating medium supplied from the three-way valve 10a to the cold supply section 5a. The controller 11a is constituted as a microcomputer. Based on a user body temperature signal produced by the sensor 13a, which is attached to a cover 12a worn by the user, the controller 11a produces a signal for controlling the three-way valve 10 to supply circulating medium at the optimum temperature to the cold supply section 5a. It also produces a signal for controlling the rotational rate of the DC compressor 6a to vary the cooling power of the heat exchanger 1a, i.e., the refrigeration capacity of the liquid cooler 9a. The cover 12a and the liquid cooler 9a of the automatic body temperature adjuster Ca are linked by a coupler (not shown). When the automatic body temperature adjuster is used outdoors, the liquid cooler 9a and the battery (not shown) used as a power source are mounted on a wheelchair.

As during outdoor use, the automatic body temperature adjuster Ca is powered by a battery mounted on a wheelchair, the automatic body temperature adjuster cannot be used outdoors continuously for more than a limited period which is determined by the battery capacity.

To overcome this limitation, it might be considered to use a battery having a large capacity. However, a battery with large capacity inevitably has increased size and weight. When such a large and heavy battery is mounted on a wheelchair, the wheelchair becomes impractically difficult to operate.

OBJECT AND SUMMARY OF THE INVENTION

The object of this invention is to provide an automatic body temperature adjuster which consumes less power and can be used continuously for an extended period of time.

In an automatic body temperature adjuster according to the invention, a cold storage material and a coolant medium circulation path for cooling the material are built into the seat and/or the back support of a wheelchair, the coolant medium circulation path being capable of being coupled by coupler means to cold supply means. The cold supply means and cold charge means comprising a heat exchanger and a circulation pump are mounted on the wheelchair. Prior to use of the automatic body temperature adjuster, the cold storage material in the seat and/or back support is cooled, i.e., cold is stored in the material, by operating the cold supply means. After use of the adjuster is commenced, the cold supply means is disconnected from the coolant medium circulation path of the seat and/or the back support and connected to the cold supply section of a cover, thereby cooling the user.

Specifically, according to the invention, there is provided an automatic body temperature adjuster which comprises a battery, cold supply means including a DC compressor operable by the battery, a condenser, an expansion valve or a capillary tube and an evaporator, these components being connected to one another in the order mentioned for circulation of a coolant medium therethrough, heat exchange means including a heat exchanger for heat exchange with respect to the evaporator, a circulation pump driven by the battery and a cold supply section for supplying cold for temperature control of a user, these components being connected to one another in the order mentioned for circulation of a coolant medium therethrough, and cold storage means provided in a seat and/or a back support of a wheelchair for storing cold, the cold storage means being provided with coupler means for connection to the heat exchange means. In use, cold is stored in advance in the cold storage means in the seat or back support by connecting the cold storage means to the heat exchange means. Thus, when the user is seated on the wheelchair and wears a cover with the cold supply section, he or she is cooled by the cover as well as from the seat and/or back support of the wheelchair. Thus, the cooling load of the liquid cooler is reduced compared with the prior art in which cooling is provided solely by the cover, the amount of this reduction being equal to the amount of cooling by the cold storage material provided in the wheelchair. The amount of power required per unit time for supplying cold is thus correspondingly reduced. This means that the battery discharge time or the period over which the automatic body temperature adjuster can be continuously used is longer for a battery of the same capacity by more than 50%.

Further, the user is cooled additionally at his or her back and/or hips so that the user is more comfortable than in the case of local cooling at the neck.

The above and other objects and features of the invention will become more apparent from the following detailed description with reference to the accompanying drawings.

DETAILED DESCRIPTION OF THE PREFERRED EMBODIMENT

A preferred embodiment of the automatic body temperature adjuster according to the invention will now be described with reference to FIGS. 1 to 7. The conventional automatic body temperature adjuster consumes much power during the cooling operation.

Figure 1:
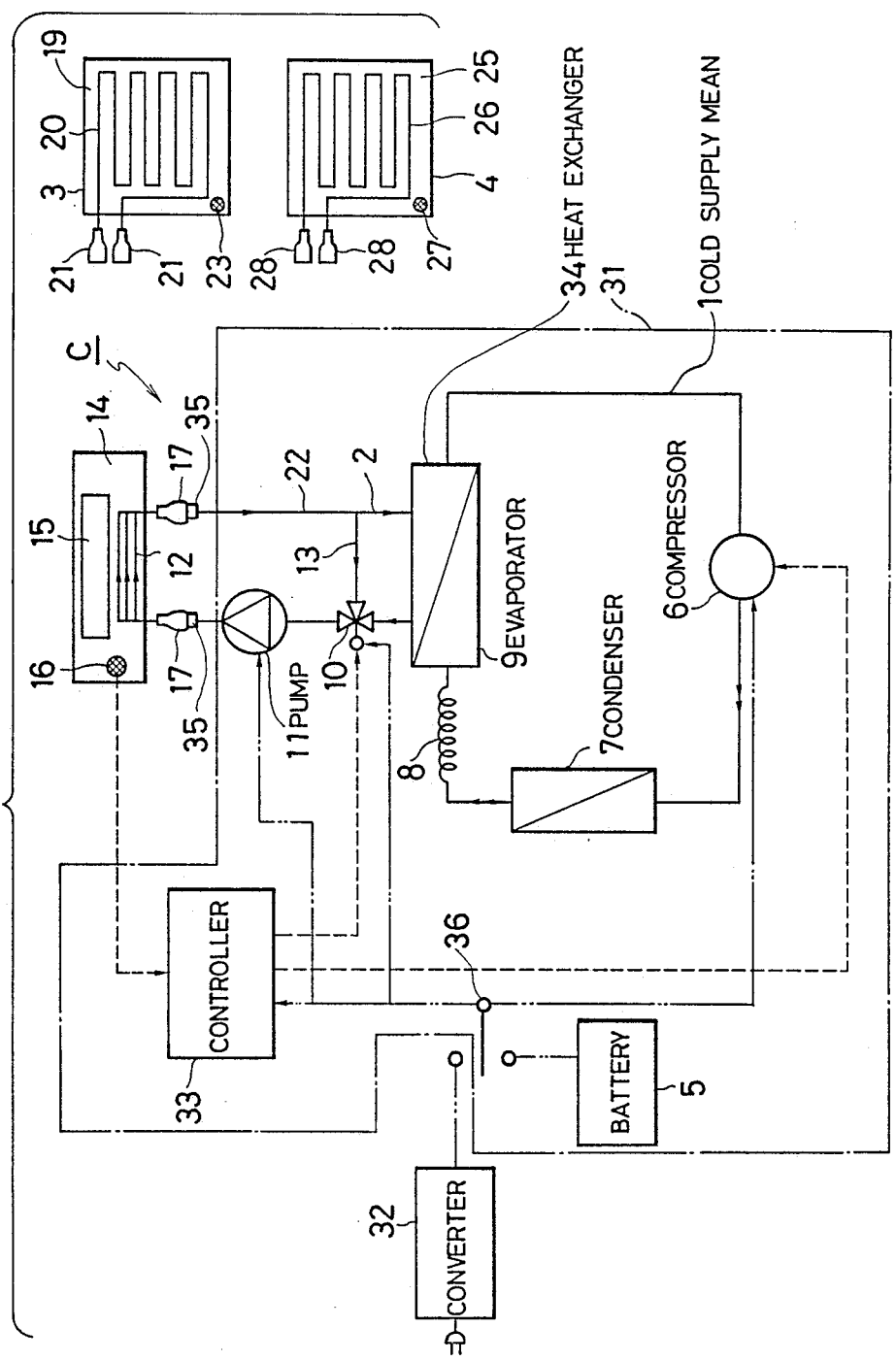
FIG. 1 is a schematic representation of one embodiment of the automatic body temperature adjuster according to the invention.

A mechanism for heat supply and heat exchange in an automatic body temperature adjuster C of the invention is shown in FIG. 1. The adjuster C comprises cold supply means 1, heat exchange means 2 and the cold storage means of a seat 3 and a back support 4 of a wheelchair.

The cold supply means 1 includes a DC compressor 6 powered by a battery 5, a condenser 7, a capillary tube 8 and an evaporator 9, these components being connected in the order mentioned to permit circulation of a coolant medium. The capillary tube 8 serves to reduce the pressure of the coolant medium which has been liquefied by cooling, and it may be replaced with an expansion valve.

Figure 2:
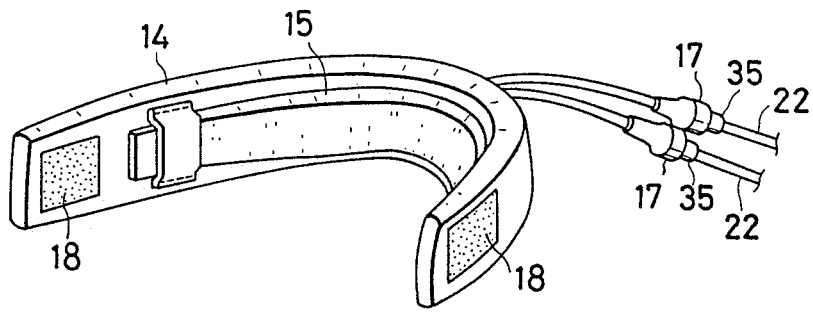
FIG. 2 is a perspective view showing a cover of the automatic body temperature adjuster.
Figure 3:
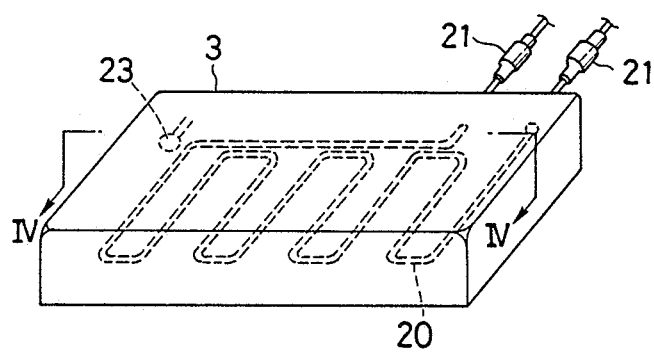
FIG. 3 is a view showing a wheelchair seat with cold storage means built therein.
Figure 4:
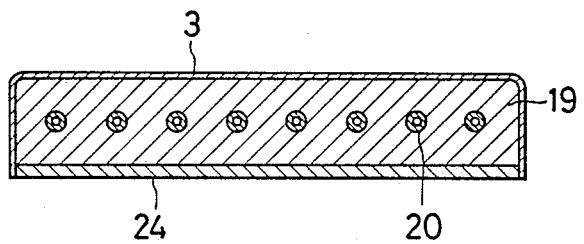
FIG. 4 is a sectional view taken along line IV—IV in FIG. 3.

The heat exchange means 2 includes a heat exchanger 34 for effecting heat exchange with respect to the evaporator 9, a three-way valve 10, a circulation pump 11 powered by the battery 5, a coolant medium circulation path 12 and a coolant medium path 22, these components being connected in the order mentioned to permit circulation of the coolant medium. It further includes a bypass 13 bypassing the heat exchanger 34 and connected to the remaining port of the three-way valve 10. As shown in FIGS. 1 and 2, the coolant medium circulation path 12 is embedded in a cover (collar) 14 which is worn on the neck of the user. The inner side of the cover 14 is provided with a cold storage member 15 and a sensor 16 for sensing the temperature of the user. The cold storage member 15 is filled with a cold storage material, e.g., an aqueous solution of sodium chloride, ethylene glycol or polyvinyl alcohol. The coolant medium path 22 of the heat exchange means 2 is provided with connectors 35, and the coolant medium circulation path 12 can be coupled and decoupled with/from the heat exchange means 2 by couplers 17 and the connector 35. Reference numeral 18 designates a fastener for holding the cover 4 worn on the user's neck.

The seat 3 of the wheelchair is typically of substantially rectangular shape. For example, it is about 400 mm wide, about 380 mm deep and about 50 mm thick. The seat 3 is filled with a cold storage material 19, e.g., an aqueous solution of sodium chloride, ethylene glycol or polyvinyl alcohol. It also includes a coolant medium circulation path 20, which carries a coolant medium for supplying cold to the cold storage material 19. The cold storage material 19 and coolant medium circulation path 20 constitute the cold storage means. The coolant medium circulation path 20 consists of tubing made of vinyl chloride for carrying water as a coolant medium. It can be connected to the circulation pump 11 and coolant medium path 22 leading to the heat exchanger 34 in the heat exchange means 2 by connecting its couplers 21 to the connectors 35 of the heat exchange means 2. Reference numeral 23 in FIG. 3 designates a sensor for sensing the temperature of the cold storage material 19 in the seat 3. The seat 3 has a bottom plate 24, which consists of a heat-insulating board (see FIG. 4).

The back support 4 of the wheelchair is typically of substantially rectangular shape. It is, for example, about 400 mm wide, about 380 mm high and about 50 mm thick. Like the seat 3, the back support 4 includes cold storage means consisting of a cold storage material 25 and a coolant medium circulation path 26. It is also provided with a sensor 27 for sensing the temperature of the cold storage material 25. The coolant medium circulation path 26 of the back support 4 can be connected to the circulation pump 11 and coolant medium path 22 leading to the heat exchanger 34 in the heat exchange means 2, when its couplers 28 are connected to the connectors 35 of the heat exchange means 2. The back support 4 has a back plate (not shown) consisting of a heat-insulating board.

Figure 5:
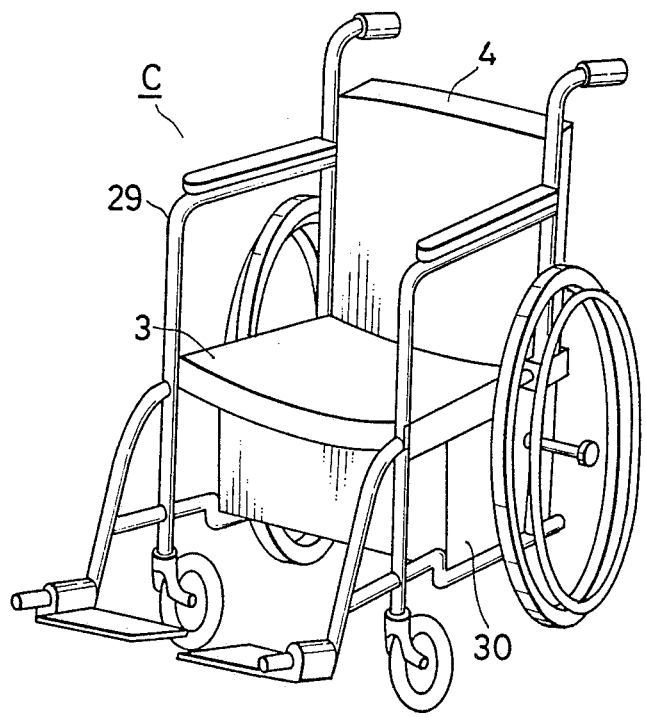
FIG. 5 is a perspective view showing a wheelchair with the automatic body temperature adjuster incorporated therein.

As shown in FIG. 5, the wheelchair 29 has a box 30 provided under the seat 3 of its body. The components shown enclosed by a single-dot-and-bar line 31 in FIG. 1 are accommodated in the box 30.

Reference numeral 32 in FIG. 1 designates a converter which converts an external AC power source voltage into a DC voltage of the same level as the voltage of the battery 5. The converter 32 can supply power to the DC compressor 6, a stepping motor (not shown) in the three-way valve 10, the circulation pump 11 and a controller 33 by operating a switch 36.

The controller 33 includes a microcomputer. Based on the output signal representing a detected temperature from the sensor 16 embedded in the cover 14, the controller 33 provides a signal for controlling the three-way valve 10 such that coolant medium of the appropriate temperature is supplied to the coolant medium circulation path 12. Also, the controller 33 provides a signal for varying the amount of cold supplied to the cold supply means 1, i.e., a signal for controlling the rate of rotation of the DC compressor 6. The controller 33 further provides a signal for controlling the rate at which coolant medium is supplied to the circulation pump 11 in the heat exchange means 2.

Figure 6:
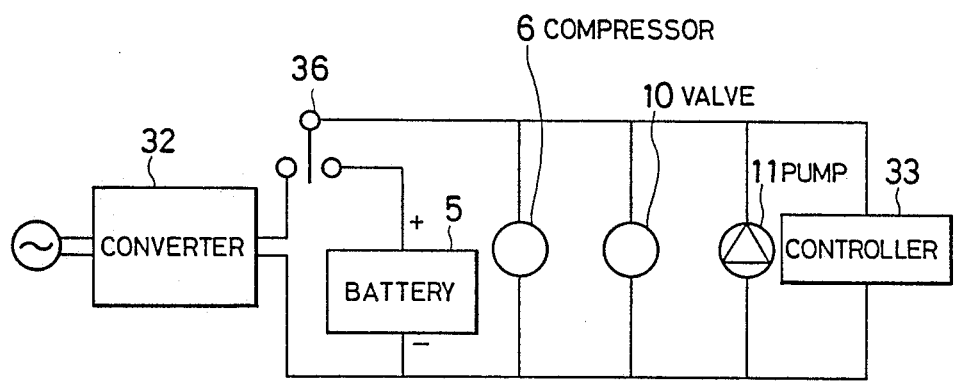
FIG. 6 is a circuit diagram showing an electric circuit of the automatic body temperature adjuster shown in FIG. 1.

FIG. 6 shows an electric circuit in the automatic body temperature adjuster C. The double-dot-and-bar line in FIG. 1 represents a power supply line.

Figure 7:
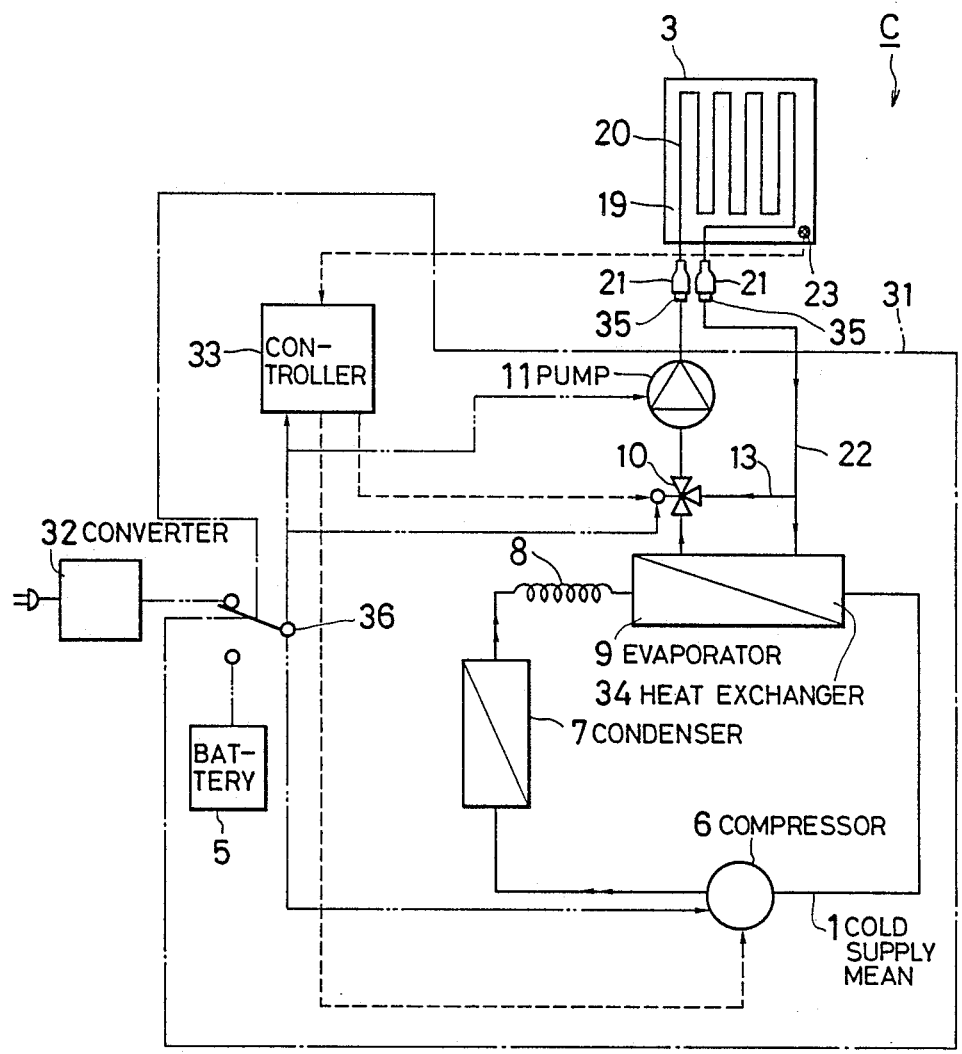
FIG. 7 is a view similar to FIG. 1 but for explaining the supply of cold to the seat of a wheelchair with the automatic body temperature adjuster shown in FIG. 1.
Figure 8:
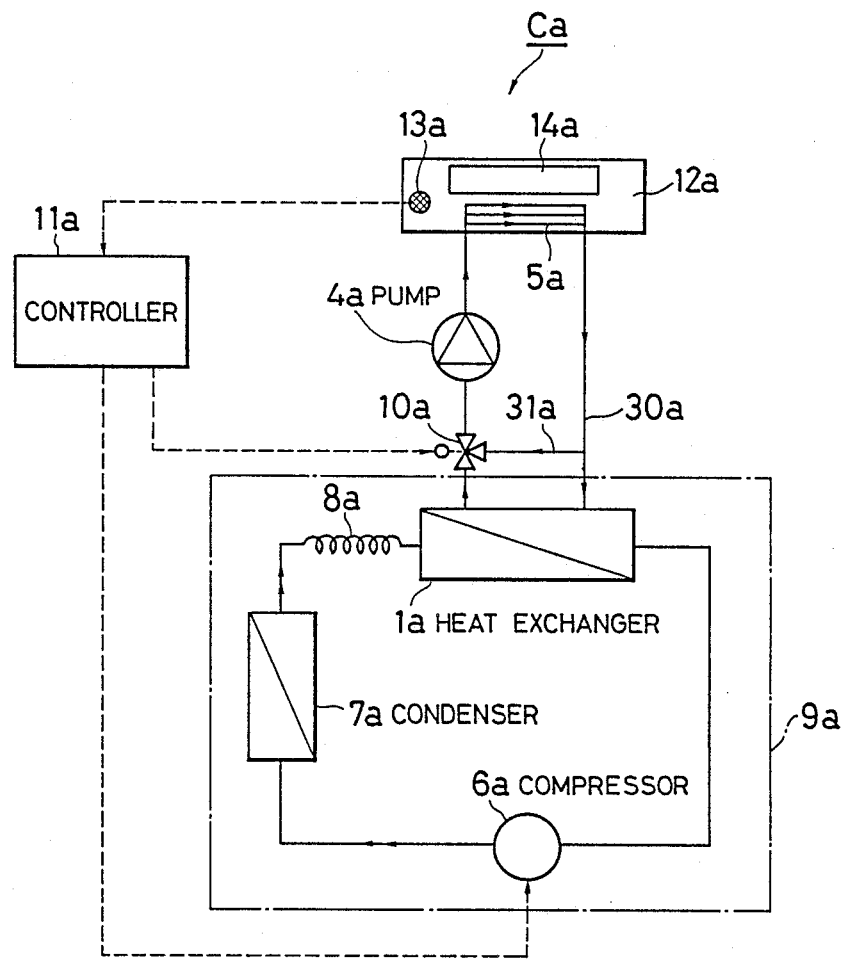
FIG. 8 is a schematic representation of a prior art automatic body temperature adjuster.

The automatic body temperature adjuster C having the above construction is used as follows. First, the coolant medium circulation path 20 of the seat 3 is connected via the couplers 21 to the connectors 35 of the coolant medium path 22 leading to the heat exchanger 34, and the sensor 23 is connected to the controller 33 as shown in FIG. 7. In this state, cold is stored in the cold storage material 19 in the seat 3 by operating the switch 36 to supply external power through the converter 32 to the DC compressor 6, three-way valve 10, circulation pump 11 and controller 33. When the cold storage material 19 has been reduced to a predetermined temperature by the coolant medium from the coolant medium path 22, the sensor 23 produces a signal for discontinuing the supply of cold to the cold storage material 19, thus completing the operation of storing cold in the cold storage means in the seat 3. When this cold storage operation has been completed, the coolant medium circulation path 20 of the seat 3 is disconnected from the coolant medium path 22 leading to the heat exchanger 34 by disengaging the couplers 21 from the connectors 35. Thereafter, cold is stored in the cold storage material 25 of the back support 4 in the same manner as with the seat 3. Afterwards, the coolant medium circulation path 12 of the cover 14 is connected to the coolant medium path 22 by the engagement of the couplers 17 with the connectors 35, the sensor 16 is connected to the controller 33, and the supply of external power from the converter 32 is cut off. This puts the automatic body temperature adjuster in stand-by state.

The user is then seated on the wheelchair 29. The user's body is thus in contact with the seat 3 and the back support 4, and the cover 14 is attached around the neck by the fasteners 18. Next, the switch 36 is operated to supply power from the battery 5 to the DC compressor 6, the three-way valve 10, the circulation pump 11 and the controller 33. When the automatic body temperature adjuster C is operated in this state, the sensor 16 senses the user's body temperature and sends a signal representing the sensed temperature to the controller 33. Upon receiving this signal, the controller 33 compares the value thereof with a preset temperature value for temperature control and, if necessary, sends signals to the DC compressor 6 and the three-way valve 10 for appropriately operating them. If it is found that the user's body has to be cooled, the compressor 6 in the cold supply means 1, in which a coolant gas medium is sealed, is operated to compress the coolant gas medium and thus increase the temperature and pressure of the gas medium. This coolant gas medium which has been elevated in temperature and pressure is supplied to a condenser 7 in which the coolant gas medium is cooled and liquefied. This liquefied medium is supplied through the capillary tube or expansion valve 8 to the evaporator 9. In the evaporator 9, the liquefied medium is evaporated. At this time, the gas extracts heat from the surroundings, thus providing a cooling function. Namely, the coolant medium which is being circulated from the heat exchanger 34 for heat exchange with respect to the evaporator 9 through the coolant medium path, is cooled. The coolant medium cooled in this way is circulated through the three-way valve 10 to the coolant medium circulation path 12 embedded in the cover 14 by the operation of the circulation pump 11. As the coolant medium is circulated to the coolant medium circulation path 12, the user's neck is cooled. Meanwhile, part of the coolant medium which has been warmed is circulated to the heat exchanger 34, and the remainder is circuited to the bypass 13.

In this operation, the amount of cold that is received by the user is the sum of the amount of cold stored in the seat 3 and back support 4 of the wheelchair and the amount of cold supplied from the coolant medium circulation path 12, which is determined by the amount of electric energy stored in the battery 5 as a source of power. This means that compared with the case where cold is supplied solely from the coolant medium circulation path 12, the amount of cold supplied to the user by the automatic body temperature adjuster C is greater by an amount corresponding to the cold stored in the seat 3 and back support 4.

The cold stored in the seat 3 and back support 4 is not dissipated instantly but is supplied gradually to the user. This means that while cold is being supplied to the user from the seat 3 and back support 4, it can be supplied at a lower rate from the coolant medium circulation path 12. Assuming that the battery 5 is charged to the same level at the initial stage of use, the remaining amount of electric charge in the battery 5 will be higher in proportion as the rate of supply of cold from the coolant medium circulation path 12 is lower. The more energy that remains in the battery 5, the longer is the period over which the DC compressor 6, the three-way valve 10, the circulation pump 11 and the controller 33 can be operated. Thus, the user can be supplied with cold for the longer period of time.

In the above embodiment, cold is stored in both the seat and back support of the wheelchair. Alternatively it is possible to store cold in only one or the other of the seat and back support.

As has been described in the foregoing, the automatic body temperature adjuster according to the invention comprises cold storage means provided in the seat and back support of a wheelchair. Thus, thanks to the cold stored in these means, the maximum period of continuous use is extended from the ordinary period of two hours for such an adjuster up to three hours or more, the actual use time being dependent to some degree on the use conditions. The user is thus able to enjoy increased mobility over a longer period of time.

Obviously, many variations and modifications of the present invention can be made in light of the above teachings. It is therefore to be understood that within the scope of the appended claims, the present invention may be practiced otherwise than as specifically described herein.

What is claimed is:

1. An automatic body temperature adjuster for use with a wheelchair, comprising:
   a seat having a coolant medium circulation path, said seat having a sensor;
   a back support having a coolant medium circulation path, said back support having a sensor;
   a collar having a coolant medium circulation path, said collar having a sensor;
   a cold supply means;
   a heat exchange means connected to said cold supply means;
   means for making said coolant medium circulation path of said seat connectable with said heat exchange means;
   means for making said coolant medium circulation path of said back support connectable with said heat exchange means;
   first control means connectable to said seat's sensor for ascertaining the temperature of said seat and regulating said cold supply and heat exchange means;
   second control means connectable to said back support's sensor for ascertaining the temperature of said back support and for regulating said cold supply and heat exchange means; and
   third control means connectable to said collar's sensor for ascertaining a person's temperature and for regulating said cold supply and heat exchange means.

2. An adjuster according to claim 1, wherein said cold supply means comprises:
   a DC compressor;
   a condensor connected to said DC compressor;
   means for reducing the pressure of a coolant medium connected to said condensor; and
   an evaporator connected to said means for reducing.

3. An adjuster according to claim 2, wherein said heat exchange means comprises:
   a heat exchanger connected to said evaporator;
   a coolant medium path connected to said heat exchanger;
   a three-way valve;
   a bypass means connecting said coolant medium path and said three-way valve; and
   a circulation pump connected to said three-way valve.

4. An adjuster according to claim 3, further comprising:
   a battery connectable to said DC compressor and to said circulation pump.

5. An adjuster according to claim 4, further comprising:
   AC to DC conversion means connectable to said DC compressor and to said circulation pump.

6. An adjuster according to claim 5, further comprising:
   switching means for alternately connecting said AC to DC conversion means and said battery to said DC compressor and said circulation pump.

7. A method for adjusting the body temperature of a person in a wheelchair, said wheelchair having a seat with a coolant medium circulation path and a back support with a coolant medium circulation path, said person wearing a collar while sitting in said wheelchair, the method comprising the steps of:
   (a) connecting the coolant medium circulation path of said seat to a heat exchange means connected to a cold supply means;
   (b) filling the coolant medium circulation path of said seat with a coolant from said cold supply means until a desired temperature is obtained in said seat;
   (c) connecting the coolant medium circulation path of said back support to the heat exchange means connected to the cold supply means;
   (d) filling the coolant medium circulation path of said back support with a coolant from said cold supply means until a desired temperature is attained in said back support;
   (e) connecting a coolant medium circulation path of said collar to the heat exchange means connected to the cold supply means;
   (f) filling the coolant medium circulation path of said collar with a coolant from said cold supply means until a desired temperature is attained in said collar.

* * * * *